(12) United States Patent
O'Brien et al.

(10) Patent No.: US 7,488,343 B2
(45) Date of Patent: Feb. 10, 2009

(54) MEDICAL DEVICES

(75) Inventors: Barry O'Brien, Barna. Co. Galway (IE);
Brian Brown, Hanover, MN (US);
Robert Nolan, Knocknacarra Co.
Galway (IE)

(73) Assignee: Boston Scientific SciMed, Inc., Maple Grove, MN (US)

( * ) Notice: Subject to any disclaimer, the term of this patent is extended or adjusted under 35 U.S.C. 154(b) by 762 days.

(21) Appl. No.: 10/664,679

(22) Filed: Sep. 16, 2003

(65) Prior Publication Data
US 2005/0060021 A1    Mar. 17, 2005

(51) Int. Cl.
*A61F 2/06* (2006.01)
(52) U.S. Cl. .................. 623/1.15; 606/108
(58) Field of Classification Search ............ 606/108; 623/1.11, 115, 1.44
See application file for complete search history.

(56) References Cited

U.S. PATENT DOCUMENTS

| | | | |
|---|---|---|---|
| 5,356,381 A * | 10/1994 | Ensminger et al. ..... 604/288.03 |
| 5,587,507 A | 12/1996 | Kohn et al. |
| 5,591,222 A | 1/1997 | Susawa et al. |
| 5,599,352 A | 2/1997 | Dinh et al. |
| 5,605,696 A | 2/1997 | Eury et al. |
| 5,624,411 A | 4/1997 | Tuch |
| 5,658,327 A | 8/1997 | Altman et al. |
| 5,697,967 A | 12/1997 | Dinh et al. |
| 5,716,981 A | 2/1998 | Hunter et al. |
| 5,725,570 A | 3/1998 | Heath |
| 5,769,883 A * | 6/1998 | Buscemi et al. ............ 623/1.42 |
| 5,776,184 A | 7/1998 | Tuch |
| 5,788,979 A | 8/1998 | Alt et al. |
| 5,800,511 A | 9/1998 | Mayer |
| 5,824,048 A | 10/1998 | Tuch |
| 5,830,217 A | 11/1998 | Ryan |
| 5,837,007 A | 11/1998 | Altman et al. |
| 5,843,172 A * | 12/1998 | Yan ........................ 623/1.42 |
| 5,869,140 A | 2/1999 | Blohowiak et al. |
| 5,873,904 A | 2/1999 | Ragheb et al. |
| 5,876,756 A | 3/1999 | Takada et al. |
| 5,888,201 A * | 3/1999 | Stinson et al. ............... 623/1.2 |
| 5,899,935 A | 5/1999 | Ding |
| 5,935,506 A | 8/1999 | Schmitz et al. |
| 5,972,027 A | 10/1999 | Johnson |
| 5,980,566 A | 11/1999 | Alt et al. |
| 6,071,305 A | 6/2000 | Brown et al. |

(Continued)

FOREIGN PATENT DOCUMENTS

AU    739507    4/1998

(Continued)

OTHER PUBLICATIONS

"Anodizing and Its Uses" Available Web Site: www.anodizing.org/AAC_FactSheet1v2.pdf Retrieved from the internet prior to the filing of the application.

(Continued)

*Primary Examiner*—Kevin T Truong
*Assistant Examiner*—Victor X Nguyen
(74) *Attorney, Agent, or Firm*—Fish & Richardson P.C.

(57) ABSTRACT

Medical devices, particularly stents, suitable for drug delivery and including a porous structure and/or colors are disclosed.

39 Claims, 8 Drawing Sheets

U.S. PATENT DOCUMENTS

| | | | |
|---|---|---|---|
| 6,096,070 | A | 8/2000 | Ragheb et al. |
| 6,099,561 | A | 8/2000 | Alt |
| 6,159,142 | A | 12/2000 | Alt |
| 6,168,602 | B1 | 1/2001 | Ryan |
| 6,180,222 | B1 | 1/2001 | Schulz et al. |
| 6,212,434 | B1 | 4/2001 | Scheiner |
| 6,214,037 | B1 | 4/2001 | Mitchell et al. |
| 6,240,616 | B1 | 6/2001 | Yan |
| 6,245,104 | B1 | 6/2001 | Alt |
| 6,253,443 | B1 | 7/2001 | Johnson |
| 6,258,117 | B1 | 7/2001 | Camrud et al. |
| 6,287,332 | B1 | 9/2001 | Bolz et al. |
| 6,290,722 | B1 | 9/2001 | Wang |
| 6,338,739 | B1 | 1/2002 | Datta et al. |
| 6,358,276 | B1 | 3/2002 | Edwin |
| 6,361,780 | B1 * | 3/2002 | Ley et al. .................... 424/400 |
| 6,368,658 | B1 | 4/2002 | Schwarz et al. |
| 6,387,121 | B1 | 5/2002 | Alt |
| 6,391,033 | B2 | 5/2002 | Ryan |
| 6,423,092 | B2 | 7/2002 | Datta et al. |
| 6,447,540 | B1 | 9/2002 | Fontaine et al. |
| 6,475,477 | B1 | 11/2002 | Kohn et al. |
| 6,478,815 | B1 | 11/2002 | Alt |
| 6,530,949 | B2 | 3/2003 | Konya et al. |
| 6,537,312 | B2 | 3/2003 | Datta et al. |
| 6,545,097 | B2 | 4/2003 | Pinchuk et al. |
| 6,589,286 | B1 | 7/2003 | Litner |
| 6,602,287 | B1 | 8/2003 | Millare et al. |
| 6,613,077 | B2 | 9/2003 | Gilligan et al. |
| 6,626,933 | B1 | 9/2003 | Lau et al. |
| 6,629,992 | B2 | 10/2003 | Bigus et al. |
| 6,663,662 | B2 | 12/2003 | Pacetti et al. |
| RE38,653 | E | 11/2004 | Igaki et al. |
| 6,884,429 | B2 | 4/2005 | Koziak et al. |
| 2001/0013166 | A1 | 8/2001 | Yan |
| 2001/0029660 | A1 | 10/2001 | Johnson |
| 2002/0004060 | A1 | 1/2002 | Heublein et al. |
| 2002/0032477 | A1 | 3/2002 | Helmus et al. |
| 2002/0035394 | A1 | 3/2002 | Fierens et al. |
| 2002/0123801 | A1 | 9/2002 | Pacetti et al. |
| 2002/0133224 | A1 | 9/2002 | Bajgar et al. |
| 2002/0165578 | A1 | 11/2002 | Sawitowski et al. |
| 2003/0044596 | A1 | 3/2003 | Lazarov et al. |
| 2003/0068355 | A1 | 4/2003 | Shanley et al. |
| 2003/0083646 | A1 | 5/2003 | Sirhan et al. |
| 2003/0088307 | A1 | 5/2003 | Shulze et al. |
| 2003/0176884 | A1 * | 9/2003 | Berrada et al. .............. 606/200 |
| 2005/0004661 | A1 | 1/2005 | Lewis et al. |
| 2007/0026038 | A1 | 2/2007 | Bayer et al. |

FOREIGN PATENT DOCUMENTS

| | | |
|---|---|---|
| CA | 2235031 | 4/1998 |
| CA | 2346857 | 5/2000 |
| CA | 2371800 | 8/2000 |
| EP | 0337035 B1 | 11/1993 |
| EP | 1 222 901 | 7/2002 |
| WO | WO 98/48851 | 11/1998 |
| WO | WO 99/64580 | 12/1999 |
| WO | WO 00/25841 | 5/2000 |
| WO | WO 00/48660 | 8/2000 |
| WO | WO 00/51136 | 8/2000 |
| WO | WO 00/66190 | 11/2000 |
| WO | WO03/094990 | 11/2003 |

OTHER PUBLICATIONS

"Anodizing Reference Guide" Available Web Site: www.anodizing.org/reference_guide.html Retrieved from the interent prior to the filing of the application.

"Current Anodizing Processes" Available Web Site: www.anodizing.org/processes.html Retrieved from the Internet prior to the filing of the application.

"Anodizing . . . The Finish of Choice" Available Web Site: www.anodizing.org/what_is_anodizing.html Retrieved from the internet prior to the filing of the application.

"Anodizing, What Is It?" Available Web Site: www.anodizing.org/definitions.html Retrieved from the internet prior to the filing of the application.

"Anodization of Titanium for Biocompatibility" Available Web Site: www.finishing.com/70/68.html Retrieved from the internet prior to the filing of the application.

"Bike Pro Buyer's Guide" Available Web Site: www.bikepro.com/products/metals/alum.html Retrieved from the internet prior to the filing of the application.

"More on Anodizing Aluminum" Available Web Site: www.turborick.com/anodize2.html Retrieved from the interent prior to the filing of the application.

List of Abstracts of References [online], 57 pages. Retrieved from: the Thomson Derwent World Patent Index.

"Best of the ACC Scientific Session 2002", *Rev Cardiovasc Med.* 2002:3(2):p. 85-104.

Brandau, W. et al., "Nanoporous Ceramic Coatings for Synthesis of Radioactive Implants," *Journal of Nuclear Medicine Abstract Book,* Jun. 7, 2000, p. 244P.

Dunn, D.S. et al., "Anodized Layers on Titanium and Titanium Alloy Orthopedic Materials for Antimicrobial Activity Applications," *Materials & Manufacturing Processes,* 7(1), p. 123-137 (1992).

Sawitowski, T. et al., "Nanoporous Alumina Coatings for Medical Implants and Stents—Radiotherapy, Drug Delivery, Biological Compatibility," Materials Research Society Symposium Proceedings, vol. 581 (1999), p. 523-528.

Sawitowski, T., "New Drug Delivery Systems—Examples of Applied Nanotechnology," p. 343-346.

Wieneke, H. et al., "Stent Coating: A New Approach in Interventional Cardiology," Herz 27,No. 6., (2002), p. 518-526.

Sawitowski, T., "New Drug Delivery Systems—Examples of Applied Nanotechnology," VDE World Microtechnologies Congress, Sep. 25-27, 2000, Expo 2000, Hannover, Germany, Proceedings vol. 1, p. 343-346.

Search Report for International Application No. PCT/US2004/030319, mailed Feb. 21, 2005.

PCT/US2004/030319 International Search Report and Written Opinion mailed Apr. 28, 2005.

Colen et al., U.S. Appl. No. 10/787,618, filed Feb. 26, 2004.

List of Abstracts of References [online], 8 pages. Retrieved from: the Thomson Derwent World Patent Index.

International Search Report and Written Opinion for International Application No. PCT/US2005/005630, mailed Jun. 22, 2005.

* cited by examiner

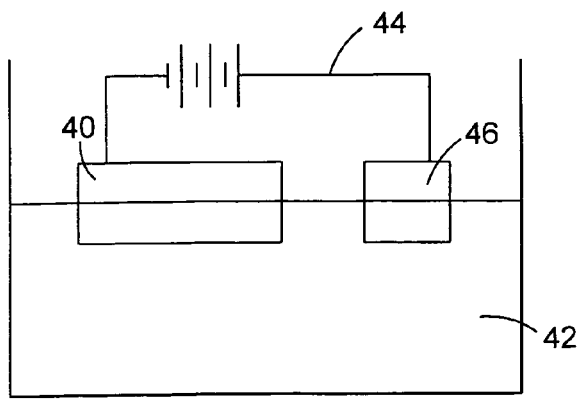
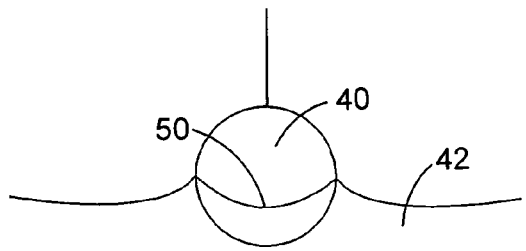
FIG. 3A
FIG. 3B
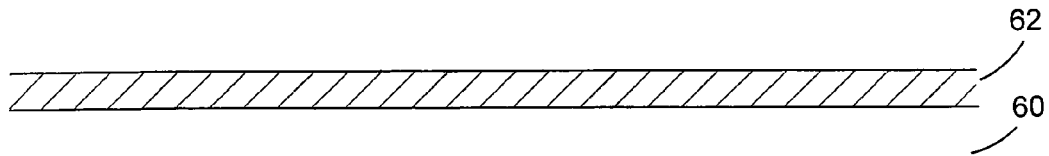
FIG. 4A
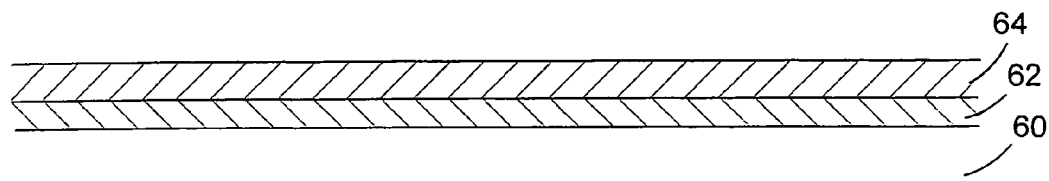
FIG. 4B

MEDICAL DEVICES

TECHNICAL FIELD

This invention relates to medical devices, such as, for example, endoprostheses.

BACKGROUND

The body includes various passageways such as arteries, other blood vessels, and other body lumens. For various treatments and diagnostic techniques, it is often desirable to deliver a medical device into these lumens. For example, these passageways sometimes become occluded or weakened. The passageways can be occluded by e.g. a tumor, restricted by plaque, or weakened by an aneurysm. When this occurs, the passageway can be reopened or reinforced, or even replaced, with a medical endoprosthesis.

An endoprosthesis is typically a tubular member that is placed in a lumen in the body. Examples of endoprostheses include stents and covered stents, sometimes called "stent-grafts". An endoprosthesis can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen. The expansion mechanism may include forcing the endoprosthesis to expand radially. For example, the expansion mechanism can include the catheter carrying a balloon, which carries the endoprosthesis. The balloon can be inflated to deform and to fix the expanded endoprosthesis at a predetermined position in contact with the lumen wall. The balloon can then be deflated, and the catheter removed.

In another delivery technique, the endoprosthesis is self-expanding. For example, the endoprosthesis can be formed of an elastic material that can be reversibly compacted and expanded. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force. Another self-expansion technique uses shape memory metals which can "remember" a particular geometric configuration, e.g. an expanded condition, upon exposure to a trigger, such as an increase in temperature.

SUMMARY

In one aspect, the invention features a stent device having a generally tubular member. The generally tubular member includes a porous structure including an oxide of titanium, niobium, or tantalum, or an alloy thereof. The porous structure includes hollow post-shaped elements.

In another aspect, the invention features a stent device having a generally tubular member. The member includes a porous structure of hollow post-shaped elements.

In another aspect, the invention features a method of making a stent. The method includes providing a metal, exposing the metal to an acid solution such that the acid solution forms a meniscus on the metal, connecting the metal as an anode in an electrical circuit in the acid solution, and applying a voltage to the circuit. The metal is incorporated in a stent.

In another aspect, the invention features a method of making a stent, the method including providing a metal, exposing the metal to an acid solution, and controlling the oxygen content of the acid solution. The method also includes connecting the metal as an anode in an electrical circuit in the acid solution, and applying a voltage to the circuit. The metal is incorporated in a stent.

In another aspect, the invention features a family of medical devices. Members of the medical devices include an oxide providing a different color or color pattern (e.g., indicative of usage).

In another aspect, the invention features a medical device including an oxide providing a color or color pattern indicative of manufacturing information (e.g., a lot, date, or manufacturer identification).

Embodiments can include one or more of the following features. The porous structure can be of an oxide of titanium. In some embodiments, the porous structure is on an outer surface of the generally tubular member. The porous structure can include a polymer that can be, e.g., a coating over the porous structure. In some cases, the coating is a diffusion or protective layer. The coating can be biodegradable. The polymer can include a therapeutic agent. In certain embodiments, the porous structure includes a colorant.

In some embodiments, the member includes a therapeutic agent. The therapeutic agent can be an antithrombogenic, antioxidant, anti-inflammatory, antiproliferative, antibiotic, drug, cell, or genetic material.

In some embodiments, the generally tubular member includes (e.g., a layer of) titanium, niobium, tantalum, or an alloy thereof. The layer can have a thickness between about 50 nm and about 500 nm. In some cases, the porous structure is over the layer. The titanium, niobium, tantalum, or alloy thereof can be a layer on a different metal. The different metal can be about 90% or more of the thickness of the tubular member. In certain embodiments, the generally tubular member includes stainless steel, nitinol, or a cobalt-based alloy (e.g., Elgiloy).

The post-shaped elements can include a porous metal oxide, e.g., on the surface of the generally tubular member. In some embodiments, the porous metal oxide has a thickness between about 50 nm and about 500 nm and/or pore diameters between about 20 nm and about 200 nm. The post-shaped elements can have a post height of about 100 nm to about 200 nm. The post-shaped elements can have pore diameters of about 20 nm to about 200 nm (e.g., about 70 nm to about 100 nm).

In certain embodiments, the device has a color corresponding to light having a wavelength between about 370 nm and about 750 nm (e.g., a wavelength of about 420 nm, about 470 nm, about 530 nm, about 580 nm, about 620 nm, or about 700 nm).

In some cases, the meniscus is formed sequentially on different portions of the metal. The acid solution can be a hydrofluoric acid solution (e.g., a 1.5% (by weight) hydrofluoric acid solution). The voltage can be about 5 V to about 100 V In some embodiments, the metal has a thickness between about 200 nm and about 400 nm.

In certain embodiments, the method includes applying a therapeutic agent and/or diffusion layer to the stent. The method can include controlling the oxygen content by bubbling gas (e.g., including oxygen) through the acid solution.

Embodiments may include one or more of the following advantages. A morphology of hollow post-shaped elements can be formed on a medical device by, e.g. anodization, to provide desired characteristics. For example, a porous structure on the surface of a medical device, such as a stent, can be a reservoir for a therapeutic material. The geometry of the porous structure, i.e. size and spacing of post-shaped elements, can be selected to, e.g., affect the rate of drug release. In addition, anodization can result in a relatively thick oxidation of a metal. The strength of the metal oxide formed by anodization can be comparable to, or even greater than, the strength of the metal. As a result, a porous oxide structure can be formed on metal body generally without substantially sacrificing the strength of the metal body on which the porous oxide structure is formed, or without impeding the function of the medical device. The robust, durable nature of the porous metal oxide structure protects it from damage during handling (e.g., during crimping, sterilizing, packaging). Furthermore, the durability of the porous metal oxide structure makes it resistant to damage from abrasion during assembly onto a catheter and delivery into the body, such that the porous structure can be relatively thin and the overall profile of the medical device is kept small. An anodized porous metal oxide can be more corrosion-resistant than the metal in its non-anodized state. A robust, porous metal oxide reservoir layer can reduce the need for, or the thickness of, drug protecting, carrying, or metering layers of polymers. To the extent a polymer coating is desirable, the surface morphology increases surface area and provides for improved bonding between the coating and the surface. The morphology can also be selected to affect the apparent color of the medical device by optical reflectance and interference phenomena. For example, a family of medical devices having, e.g., different sizes, therapeutic agents, or other features can be color-coded by varying the surface morphology. Anodization is effective to vary surface morphologies of metals that have desirable characteristics such, as biocompatibility, radiopacity, and MRI visibility. Particularly advantageous porous structures can be formed in titanium, niobium, or tantalum, and alloys including these metals, which can be used to make a medical device, or which can be coated on another material (metal, ceramic, polymer) from which the medical device, or a component of the medical device, is made. A desired morphology can also reduce thrombosis by surface roughness, surface charge, and/or metal ion release.

Still further aspects, features, and advantages follow.

DESCRIPTION OF DRAWINGS

FIGS. 2A and 2B are greatly enlarged cross sections through the side wall of a stent, while

FIG. 3A is a schematic of an anodization apparatus.

FIG. 3B is a front view of a stent in the anodization apparatus of FIG. 3A.

FIGS. 4A-4E are schematics of a surface treatment process.

DETAILED DESCRIPTION

Structure

Figure 1A:
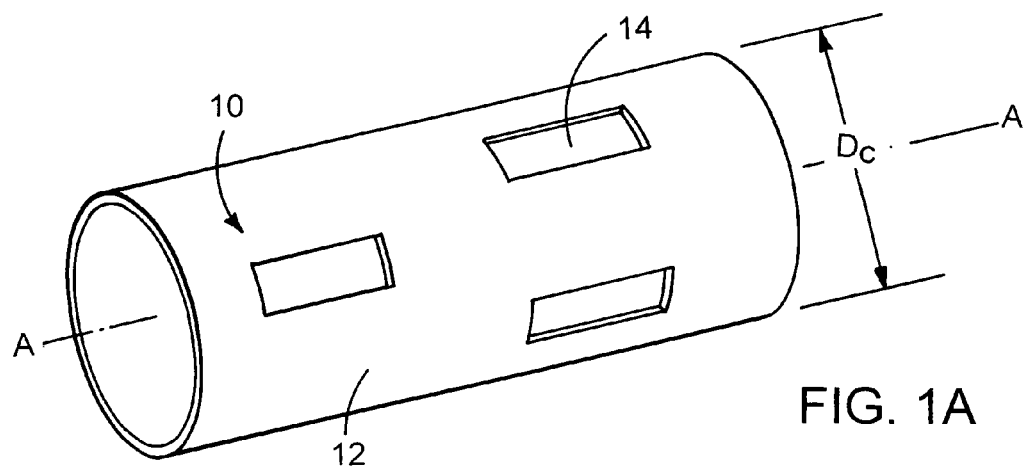
FIGS. 1A and 1B are perspective views of a stent in the compressed and expanded condition, respectively.
Figure 1B:
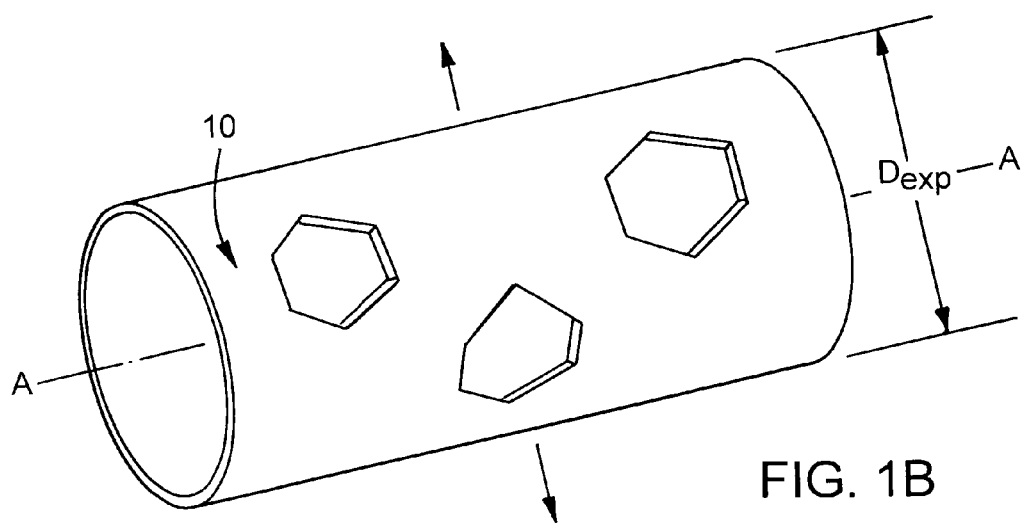

Referring to FIGS. 1A and 1B, a stent 10 includes a metal body 12 in the shape of a tube. The metal body includes aperture regions 14 provided in a pattern to facilitate stent functions, such as radial expansion, and lateral flexibility. Referring particularly to FIG. 1A, for delivery into the body, the stent 10 is provided or maintained in a relatively small diameter condition corresponding to a diameter $D_c$. Referring to FIG 1B, upon placement at the treatment site, the stent 10 is expanded to a larger diameter, $D_{exp}$, so that the stent is in contact with the lumen wall. The stent may be expanded by a mechanical expander, such as an inflatable balloon, or it may be self-expanding. The metal body of the stent may be formed by a generally continuous sheet or by filaments that are wrapped, braided, knitted or otherwise configured to generally define a stent. A suitable stent design is the Express stent, available from Boston Scientific, Natick, Mass. Balloon expandable and self-expanding stents are further discussed in Heath, U.S. Pat. No. 5,725,570, the entire contents of which are incorporated herein by reference.

Figure 2A:
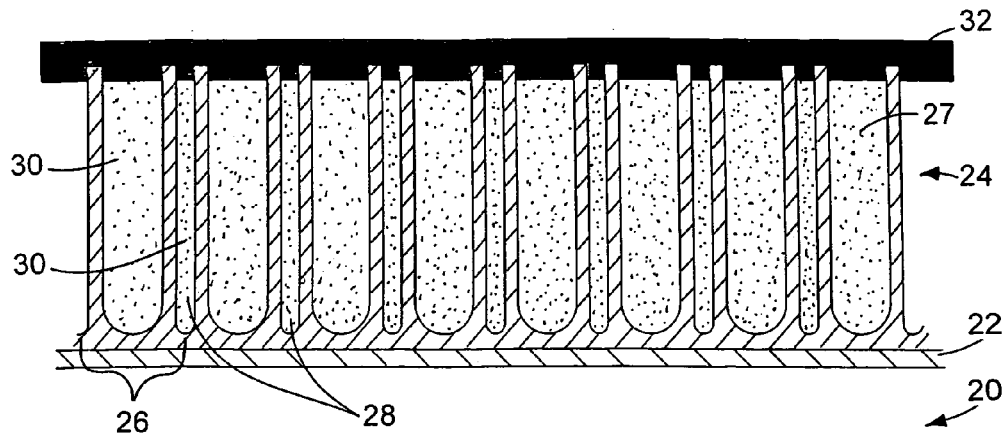
Figure 2B:
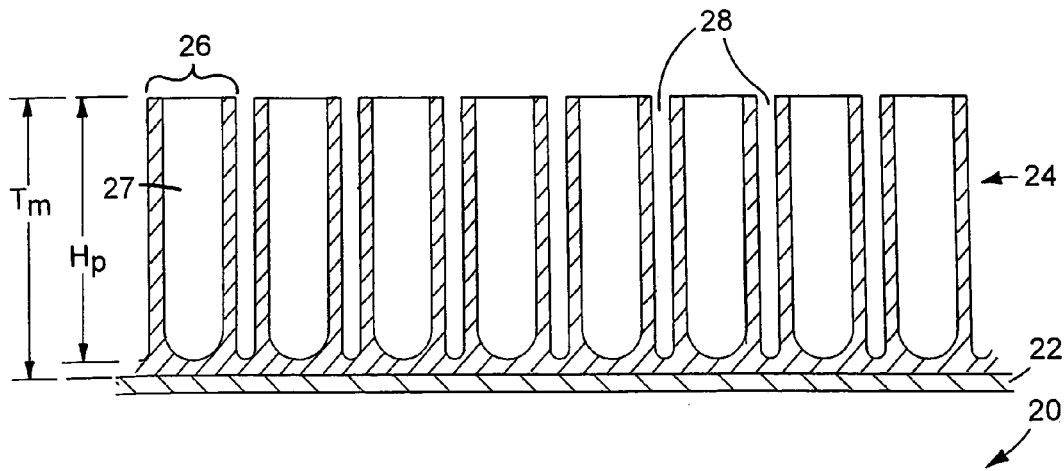

Referring to FIGS. 2A and 2B, greatly expanded cross-sections through the side wall of a stent, the stent side wall is composed of a base material 20, an intermediate layer 22, and a porous layer 24. The porous layer 24 has a morphology characterized by hollow post-shaped elements 26. The hollow post-shaped elements 26 define internal volumes 27. Between post-shaped elements 26 are void regions 28. Referring particularly to FIG. 2A, the internal volumes 27 and void regions 28 contain a therapeutic agent 30. A protective or diffusion layer 32 is provided over and within the surface openings of the porous structure. Suitable protective layers include bio-erodible polymers which protect the therapeutic agent from exposure to body fluids for a time period based on the thickness and erosion rate of the polymer. Suitable diffusion layers include porous polymers that control the rate of diffusion from the reservoir. In embodiments, a therapeutic agent in the reservoir can be combined in a matrix of erodible polymer.

Figure 2C:
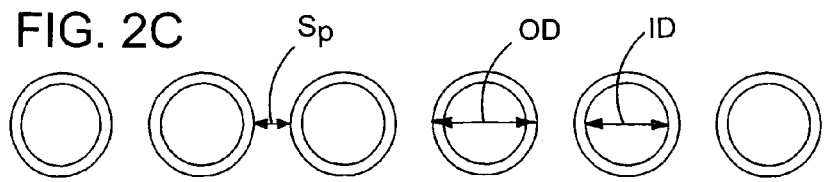
FIG. 2C is a top view of a portion of the stent side wall shown in FIGS. 2A and 2B.

Referring particularly to FIGS. 2B and 2C, the morphology of the porous layer 24 can be selected to enhance therapeutic agent delivery or other characteristics. For example, the porous morphology can be characterized by the internal volume of the hollow post-shaped elements, the voids between hollow post-shaped elements, and/or the density of the post-shaped elements, which affect the amount of therapeutic agent that can be delivered. The inner diameter or aspect ratio of the post-shaped elements and/or the size of the voids can be varied, which affects the diffusion rate from the reservoir. Pores of different sizes can exhibit different light interference and reflection patterns, thereby resulting in different natural colors.

A hollow post-shaped morphology can be characterized by a thickness $T_m$, height $H_p$, and a spacing $S_p$ between post-shaped elements. In embodiments, height $H_p$ is about 100 nm to about 200 nm, and spacing $S_p$ is about 1 nm to about 200 nm (e.g., a typical spacing is about 10 nm to about 180 nm). As shown in FIG. 2C, post-shaped elements 26 have an outer diameter OD and an inner diameter ID. Outer diameter OD is about 20 nm to about 250 nm. Inner diameter ID is about 5 nm to about 200 nm (e.g., about 70 nm to about 100 nm). The wall thickness of the tube-shaped elements, measured at the top of the elements, is, for example, about 5 nm to about 50 nm.

In embodiments, the porous layer 24 has a post-shaped element density of about 10 to about 300 post-shaped elements per square micron. In embodiments, the post-shaped element density is different in different parts of the porous layer. The percentage of open area on the layer (i.e., the space on which there are no post-shaped elements) can be about 50% to about 99%. In embodiments, a porous layer has a certain color or colors. For example, an anodized titanium surface can appear to be a specific color because of the size of its pores, and their light reflection and interference patterns. In embodiments, a morphology defined by an array of post-shaped elements acts as a grating that preferentially reflects light of a particular color. In other embodiments, an anodized surface can vary color by thin film effects, e.g., when the surface is a continuous oxidized layer, rather than discrete post-shaped elements. The porous layer may produce a color corresponding to light having a wavelength between about 370 nm and about 750 nm. The color of the porous layer can, for example, correspond to light having a wavelength of about 420 nm, about 470 nm, about 530 nm, about 580 nm, about 620 nm, or about 700 nm. In other embodiments, the color can be in the infrared or ultraviolet range. Coloring agents such as dyes can be added into the porous layer. A sealing layer (e.g., a polymer) can be formed over the porous layer to protect the coloring agent. Alternatively, the pores can be sealed by treating the porous layer with boiling water. The color of the porous layer can be used to indicate the type of therapeutic agent in a stent, for example. The color can indicate the specific dose of therapeutic agent or its release rate. In embodiments, the color can be an indication of the specific purpose for the stent (e.g., a coronary stent). Different portions of a stent can have different colors. The colors can be provided in a pattern to indicate, e.g., manufacturing information (e.g., manufacturing lot or date, and/or manufacturer's logo), or usage indication.

The porous layer, intermediate layer and stent body can be made of metal or metal oxide. The metals or metal oxides of the layers can be the same or different. Suitable metals include, e.g., titanium, tantalum, niobium, and aluminum, in substantially pure elemental form or in alloys. In particular embodiments, the stent body can be stainless steel or nitinol. Titanium, niobium, and tantalum are particularly desirable because of their high biocompatibility. Tantalum and niobium are particularly desirable for their radiopacity and MRI visibility. In a particular embodiment, the stent body is made of stainless steel, nitinol, or another metal with desirable strength and flexibility characteristics, the intermediate layer is non-porous titanium, tantalum, or niobium, and the porous layer is oxidized titanium, tantalum or niobium. The base metal provides most of the thickness of the stent wall, e.g., about 90% or more. In some embodiments, the stent body is porous but a surface layer is nonporous. In some cases, the stent body itself is made of an anodizable metal (e.g., titanium, tantalum, niobium, or alloys thereof), and is treated as described with reference to FIGS. 3A and 3B, infra.

Manufacture

Referring to FIGS. 3A and 3B, the hollow post-shaped porous morphology can be formed by anodization. In anodization, a work piece such as a stent 40 is placed in a chemical bath 42 and connected as the anode of an electrical circuit 44 to induce surface oxidation. The stent can, for example, be oriented horizontally or vertically, and then dipped into the chemical bath. The cathode 46 of the circuit can be, e.g., titanium or graphite. In embodiments, several (e.g., three, four, five) cathodes 46 can surround stent 40 to enhance current distribution across the surface of stent 40.

Referring particularly to FIG. 3B, the process parameters, such as exposure time to the chemical bath and oxygen consumption/aeration, can be controlled to effect a desirable hollow post-shaped morphology by anodizing at a meniscus. The stent 40 is partially immersed in the chemical bath 42. At the interface of the bath and the atmosphere, a meniscus 50 forms on the surface of the stent. The exposure time of a portion of the stent to the meniscus can be varied by moving the stent relative to the bath, e.g., by rotating the stent about its axis, while anodization is conducted. As illustrated in the examples below, anodization at the meniscus can be used to form well-defined morphologies of hollow post-shaped elements on metals such as titanium.

The depth, diameter, and spacing of the post-shaped elements can be controlled by controlling process parameters such as the process time, exposure depth, and oxygen consumption/aeration in the chemical bath, the composition of the chemical bath, circuit voltage, process temperature, and the metal undergoing treatment. If low acid concentrations and temperatures are used, then the resulting anodized surface may be less porous and harder than it is if higher temperatures and acid concentrations are used. Higher temperatures, higher acid concentrations, and longer anodization time periods can produce more porous and, in some cases, softer, coatings. The chemical bath includes an acid solution. Particular acids include strong acids such as hydrogen halides, e.g., HF or HCl, and phosphoric and sulfuric acids and mixtures thereof.

The circuit voltage can influence the size of the openings of the hollow post-shaped elements. For example, higher voltages yield larger openings. The circuit voltage is typically in the range of about 5 V to about 100 V, e.g., about 20 V to about 80 V. The temperature for the anodization process can be equal to or greater than about 10° C. (e.g., between about 10° C. and about 70° C., between about 20° C. and about 60° C.). In a particular example, the chemical bath can be an acid solution, such as a hydrofluoric acid solution (e.g., a 1.5% by weight hydrofluoric acid solution), a phosphoric acid solution (e.g., a 20% by volume phosphoric acid solution), or a sulfuric acid and phosphoric acid solution (e.g., a 10% by volume sulfuric acid and 80% by volume phosphoric acid solution). The circuit voltage can be, e.g., between about 5 V and about 100 V (e.g., about 20 V or about 80 V). For example, the temperature for the anodization process can be about 25° C. Exposure time to the chemical bath can be less than about one minute (e.g., between about five seconds and about ten seconds).

In the embodiments described above, anodization is carried out at the meniscus to form an anodized surface of post-like structures. The oxygen level available to the anodized region can also be varied using other techniques (e.g., oxygen or air can be bubbled through the chemical bath). In embodiments, an entire surface to be anodized (e.g., a stent) can be immersed in the chemical bath, rather than being anodized at the meniscus.

Figure 4C:
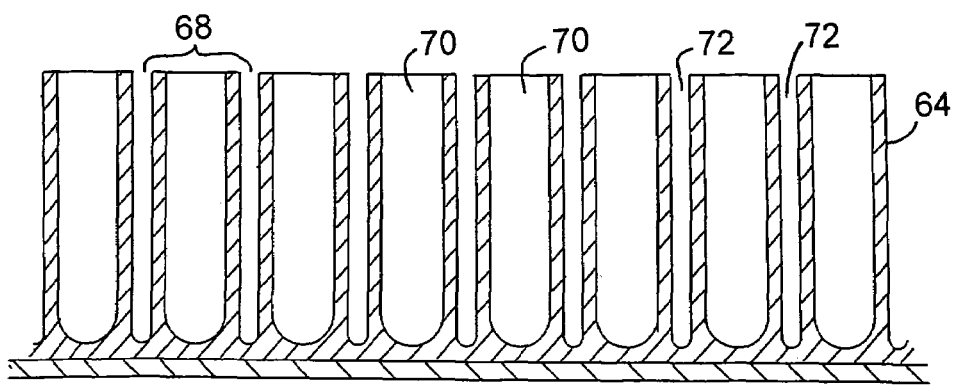

Referring to FIGS. 4A-4E, a stent-forming process is illustrated. In FIG. 4A, a base material 60 is provided. The base material may be a metal, such as stainless steel, that forms the body of the stent. The thickness of the body is typically about 0.005 mm or more, e.g., about 0.05 mm to about 0.3 mm. An anodizable metal is provided as a surface layer 62 on the stent. The surface layer can be provided by techniques including physical vapor deposition, chemical vapor deposition, spraying, electroplating, dipping, or combinations of these processes. The surface layer preferably is provided by physical vapor deposition. The deposited layer is typically near the full density of the metal, e.g., between about 90% and about 100% (e.g., about 99%) the density of the full metal. The deposited layer does not exhibit significant or regular porosity. In embodiments, the thickness of the deposited layer is typically in the range of about 10% or less of the thickness of the stent body. In embodiments, the thickness of the layer is about 0.1 micron to about 1.0 micron. The layer can be provided on just the exterior wall surface of the stent, just the interior surface, or both the interior and exterior surfaces. The layer can completely cover the stent surface or just portions of the surface.

Referring to FIG. 4B, the surface layer 62 is anodized. Anodization oxidizes the surface layer, thereby creating porous layer 64 having a morphology of hollow post-shaped elements. For example, if the surface layer is titanium, then anodization creates a titanium oxide layer.

Referring to FIG. 4C, a greatly enlarged cross-sectional view of FIG. 4B, the anodization process creates a porous layer 64 that exhibits a desired porosity. Porous layer 64 has post-shaped elements 68 defining internal volumes 70. Post-shaped elements 68 are separated by void regions 72. Porous layer 64 can exhibit enhanced surface toughness relative to the material from which it is formed. The porous layer can be provided over the entire stent or over portions of the stent, e.g., the exterior surface.

Figure 4D:
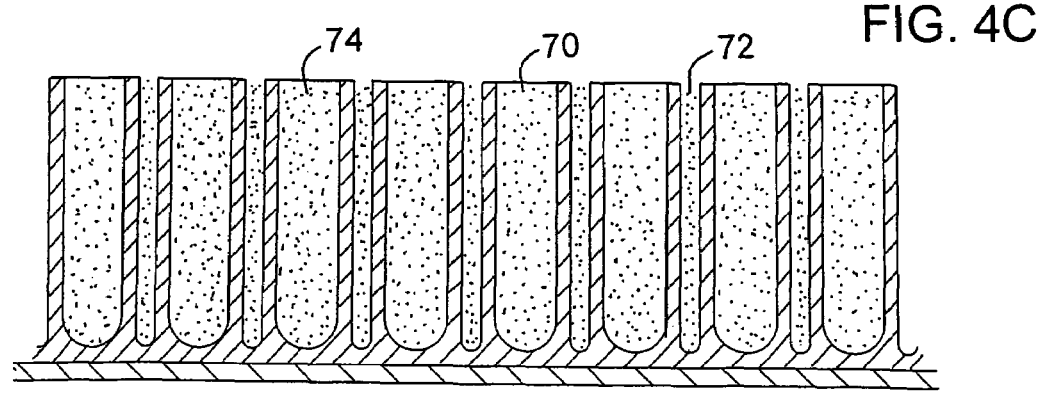

Referring to FIG. 4D, a material such as a therapeutic agent can be provided into the porous structure by, for example, dipping, spray coating or the like. The therapeutic agent can be provided into the volumes and void regions defined by the post-shaped elements. In FIG. 4D, a therapeutic agent 74 has been delivered into both the internal volumes of the post-shaped elements 70 and the void regions 72.

Figure 4E:
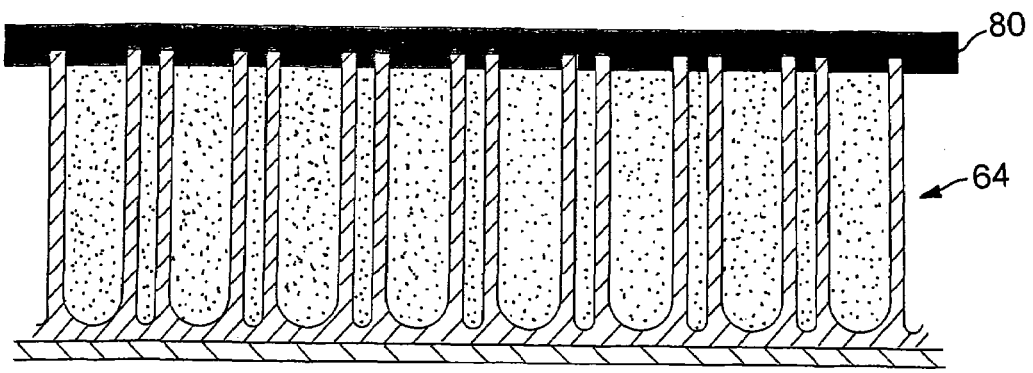

Referring to FIG. 4E, the porous layer 64 can be coated with a protective or diffusion layer 80. In some cases, the protective layer also is a diffusion layer. The protective and/or diffusion layer can be within each pore or can cover the entire stent.

The protective layer can be a biodegradable material that protects and retains the therapeutic agent in the porous structure prior to delivery into the body. For example, the protective layer can be a polymer, e.g. polytetrafluoroethylene (available from DuPont under the tradename Teflon®). The thickness of the protective layer can be between about 0.1 µm and about 10 µm. The protective layer can be an erodible polymer. Suitable erodible polymers include water soluble polymers such as polyvinyl alcohol (e.g., that has not been cross-linked), hydrogels (e.g., polyacrylic acid, haluronic acid, gelatin, carboxymethyl cellulose), polyethylene glycols (PEG), chitosan, and polyesters (e.g., polycaprolactones).

The diffusion layer controls the release of the therapeutic agent out of the pores. The diffusion layer can be biodegradable. Alternatively or additionally, the diffusion layer can be a polymer. Polymers may be, for example, homopolymers or copolymers, crosslinked or uncrosslinked, linear or branched, natural or synthetic, thermoplastic or thermosetting. Polymers include the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, styrene polymers and copolymers such as polystyrenes, styrene-maleic anhydride copolymers, styrene-butadiene copolymers, styrene-ethylene-butylene copolymers (e.g., a polystyrene-polyethylenelbutylene-polystyrene (SEBS) copolymer, available as Kraton® G series polymers), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS, see, e.g., U.S. Pat. No. 6,545,097), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters)such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and additional copolymers of the above.

Examples of polymers include block copolymers comprising at least one A block and at least one B block. The A blocks are preferably soft elastomeric blocks, which are based upon one or more polyolefins, or other polymer with a glass transition temperature at or below room temperature. For example, the A blocks can be polyolefinic blocks having alternating quaternary and secondary carbons of the general formulation: —(CRR'—CH$_2$)$_n$—, where R and R' are, independently, linear or branched aliphatic groups such as methyl, ethyl, propyl, isopropyl, butyl, isobutyl and so forth, or represent cyclic aliphatic groups such as cyclohexane, cyclopentane, and the like, either with or without pendant groups. Preferred polyolefinic blocks include polymeric blocks of isobutylene,

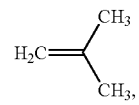

(i.e., polymers where R and R' are methyl groups). Other examples of A blocks include silicone rubber blocks and acrylate rubber blocks.

The B blocks are preferably hard thermoplastic blocks with glass transition temperatures significantly higher than the elastomeric A blocks which, when combined with the soft A blocks, are capable of, inter alia, altering or adjusting the hardness of the resulting copolymer to achieve a desired combination of qualities. Examples of B blocks include polymers of methacrylates or polymers of vinyl aromatics. More specific examples of B blocks include blocks that are (a) formed from monomers of styrene

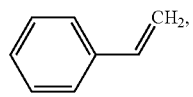

styrene derivatives (e.g., α-methylstyrene, ring-alkylated styrenes or ring-halogenated styrenes or other substituted styrenes where one or more substituents are present on the aromatic ring) or mixtures of the same, collectively referred to herein as "styrenic blocks" or "polystyrenic blocks" or are (b) formed from monomers of methylmethacrylate, ethylmethacrylate, hydroxyethyl methacrylate or mixtures of the same.

The block copolymers are provided in a variety of architectures, including cyclic, linear, and branched architectures. Branched architectures include star-shaped architectures (e.g., architectures in which three or more chains emanate from a single region), comb architectures (e.g., copolymers having a main chain and a plurality of side chains), and dendritic architectures (including arborescent or hyperbranched copolymers).

Some specific examples of such block copolymers include the following: (a) BA (linear diblock), (b) BAB or ABA (linear triblock), (c) B(AB)$_n$ or A(BA)$_n$ (linear alternating block), or (d) X-(AB)$_n$ or X-(BA)$_n$ (includes diblock, triblock and other radial block copolymers), where n is a positive whole number and X is a starting seed, or initiator, molecule. One specific group of polymers have X-(AB)$_n$ structures, which are frequently referred to as diblock copolymers and triblock copolymers where n=1 and n=2, respectively (this terminology disregards the presence of the starting seed molecule, for example, treating A-X-A as a single A block, with the triblock therefore denoted as BAB). A particularly beneficial polymer from this group is polystyrene-polyisobutylene-polystyrene triblock copolymer (SIBS). Where n=3 or more, these structures are commonly referred to as star-shaped block copolymers. Other examples of block polymers include branched block copolymers such as dendritic block copolymers, wherein at least one of the A and B blocks is branched, for instance, where the A blocks are branched and are capped by the B blocks.

The thickness of the diffusion layer can be, e.g., between about 0.1 μm and about 10 μm.

The porous layer can be partially sealed to control drug diffusion. A partial sealant layer can be added to the porous layer, or the porous layer can be partially sealed by treating the porous layer with boiling water. During such treatment, the oxide is hydrated, causing it to swell and thereby start to close in the pores. The parameters of the sealing process can be adjusted to achieve a desired amount of sealing.

The protective layer, diffusion layer, or sealant layer can include a therapeutic agent instead of or in addition to a therapeutic agent in the porous layer. The therapeutic agent in these layers can be the same as or different from the therapeutic agent in the porous layer. For example, the protective, diffusion, or sealant layer can include an antithrombogenic agent, which is released quickly during delivery and deployment, while the porous layer contains an anti-inflammatory, which is released more slowly at the site. The therapeutic agent provided in the volumes and voids of the porous layer can be dissolved in a carrier, such as an erodible polymer or a diffusion-controlling polymer.

The term "therapeutic agent" includes one or more "therapeutic agents" or "drugs". The terms "therapeutic agents" and "drugs" are used interchangeably and include pharmaceutically active compounds, nucleic acids with and without carrier vectors such as lipids, compacting agents (such as histones), virus (such as adenovirus, adeno-associated virus, retrovirus, lentivirus and a-virus), polymers, antibiotics, hyaluronic acid, gene therapies, proteins, cells, stem cells and the like, or combinations thereof, with or without targeting sequences. Specific examples of therapeutic agents include, for example, pharmaceutically active compounds, proteins, cells, stem cells, oligonucleotides, ribozymes, antisense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a noninfectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/anti-proliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, dephalosporins, aminoglycosides, and nitorfurantoin; anesthetic agents such as lidocaine, buplvacaine, and ropivacaine; nitrix oxide (NO) donors such as lisidomine, molsidomine, L-argine, NO-protein adducts, NO-carbohydrate adducts, polymeric or oligomeric NO adducts; anti-coagulants such as D-Phe-Pro-Arg chloromethyl ketone, an RGD peptide-containing compound, heparine, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability.

Stent Delivery

Figure 5A:
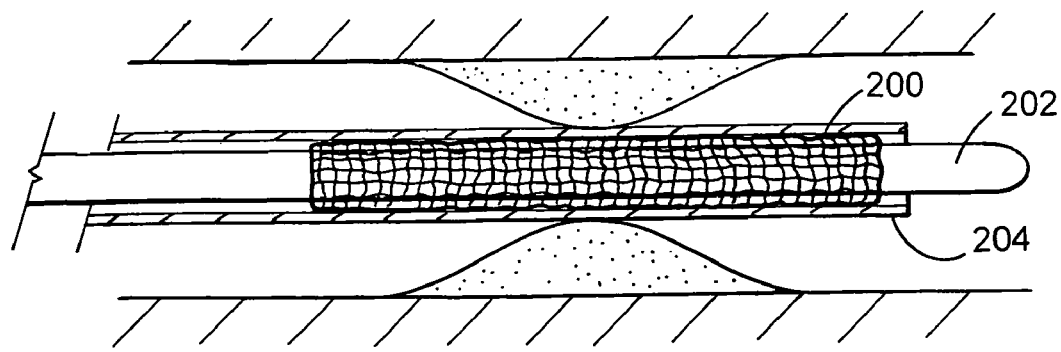
FIGS. 5A-5C illustrate delivery of a self-expanding stent.
Figure 5B:
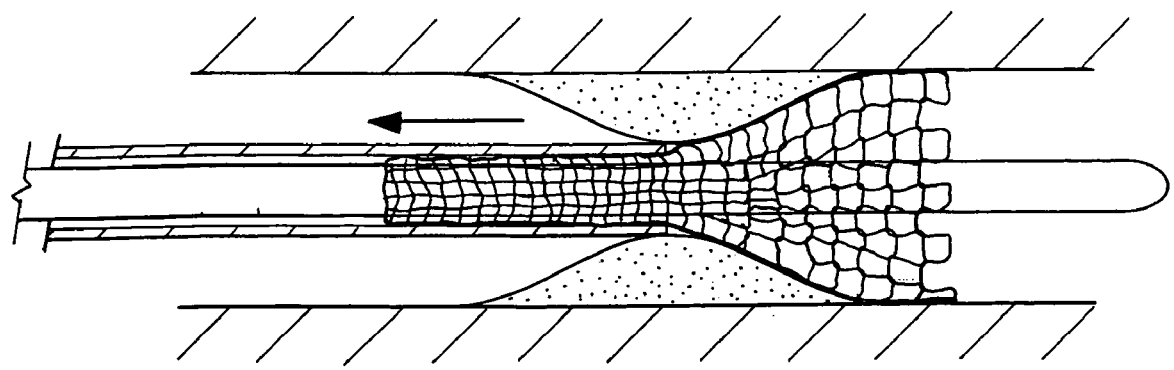
Figure 5C:
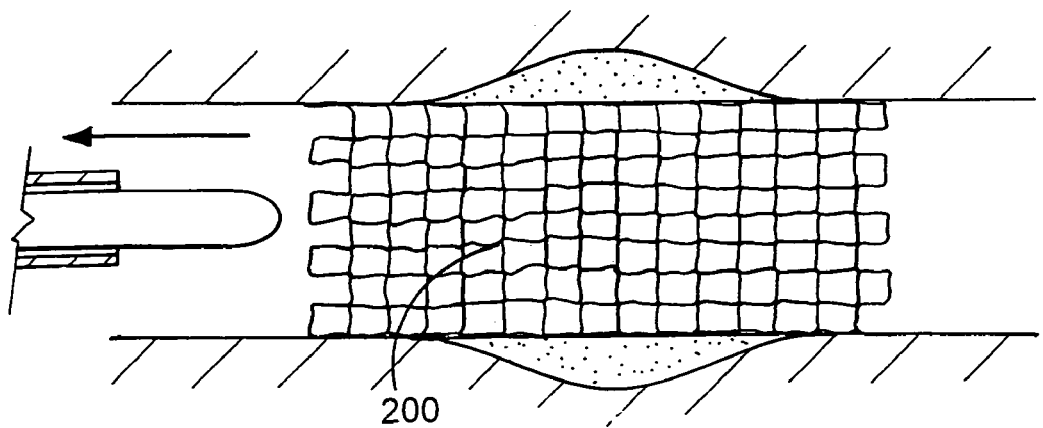

Referring to FIGS. 5A-5C, the delivery of a self-expanding stent is illustrated. The stent 200 is deployed on a catheter 202 and covered by a sheath 204. When the target site is reached, the sheath is retracted and the stent self-expands into contact with the body lumen.

Figure 6A:
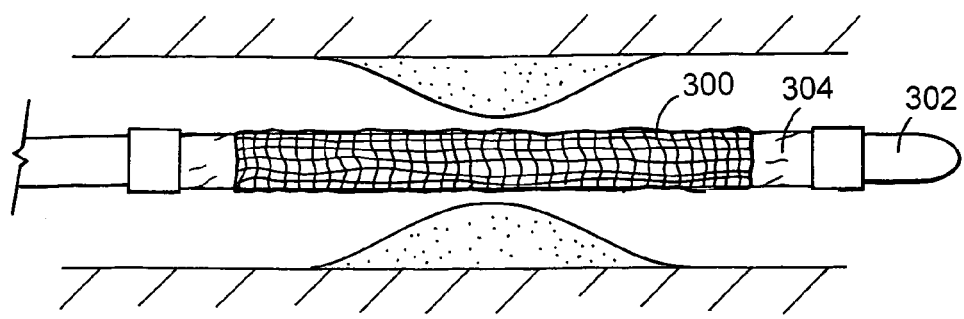
FIGS. 6A-6C illustrate delivery of a balloon expandable stent.
Figure 6B:
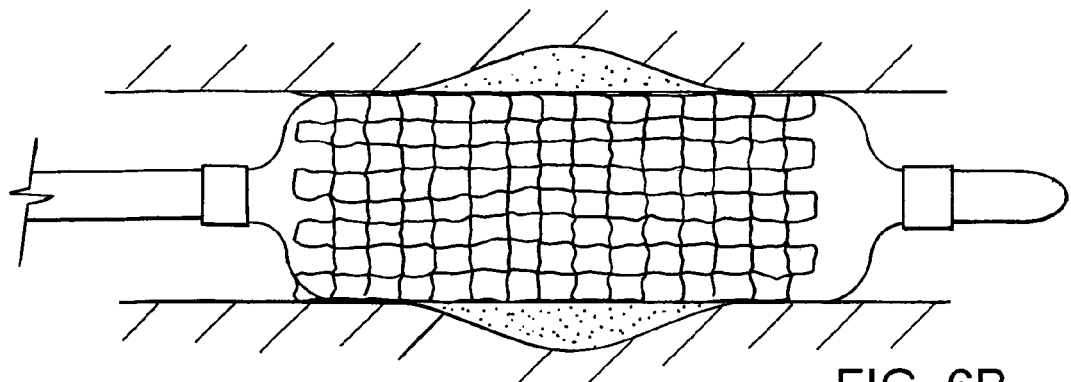
Figure 6C:
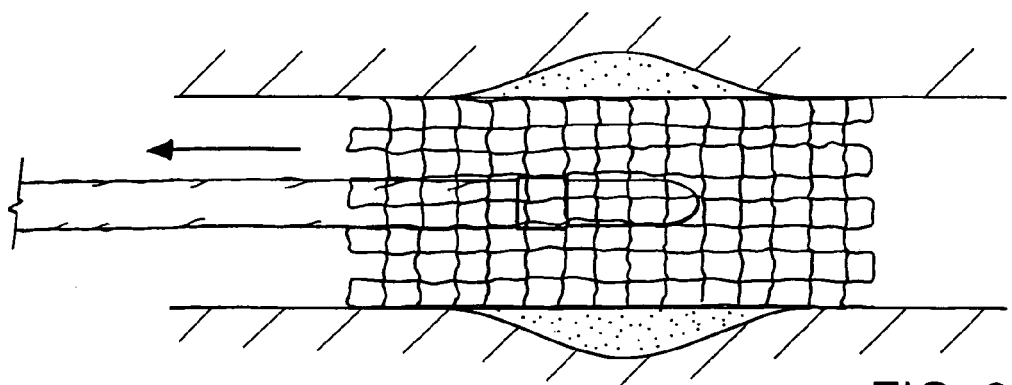

Referring now to FIGS. 6A-6C, the delivery of a balloon-expandable stent is illustrated. The stent 300 is carried on a catheter 302 over a balloon 304. When the treatment site is reached, the balloon is expanded to expand the stent into contact with the lumen wall.

The stent body may be made of, for example, Nitinol, a nickel-titanium alloy that can provide the stent with super-elasticity and shape memory properties. In some cases, the stent body may be made of stainless steel (e.g., 300 series stainless steel), or aluminum. In some embodiments, the stent body may be made of tantalum, niobium, titanium, or alloys thereof. The stent body may be made of composite materials as described in Heath, U.S. Pat. No. 5,725,570, and Mayer, U.S. Pat. No. 5,800,511. In some cases, the stent body may be made of a cobalt-based alloy, such as the cobalt-based alloys sold under the tradenames Elgiloy (available from Carpenter Technology Corporation, Reading, Pa.), Phynox (available from Metal Imphy, Imphy, France), and MP35N (available from Carpenter Technology Corporation, Reading, Pa.). A stent as described above has applications, including, for example, in the vascular system (e.g., in the coronary arteries), or in the gastrointestinal tract. The stent may be an esophageal stent. The stent may be used in the biliary duct, or in other body lumens.

EXAMPLES

Experimental

The anodizing process for titanium is first illustrated using flat sheet coupons of 99.6+% pure titanium (25×25×0.5 mm). A DC power source is used, with the coupon connected up as the anode. The coupon is suspended into the solution, not fully immersed as the electrical connection is through a crocodile clip. The cathode used is also a piece of titanium, though a graphite electrode is used for some experiments. Anodizing is performed using the following different solutions:

20% Phosphoric Acid
80% Phosphoric Acid, 10% Sulfuric Acid
1.5% (wt) Hydrofluoric Acid Voltages range from 5 V up to 100 V. Typically color/oxide develops within the first few seconds of the process i.e. usually in much less than one minute—as the oxide develops and thickens the current flow drops rapidly due to the increase in resistance. Coupons are removed, rinsed in deionized water and then alcohol, and dried. The color obtained is documented and a selection of samples are examined optically and on field emission SEM.

A number of titanium coated stents are also anodized, at 80 V in the phosphoric acid solution. The stents initially have an outer layer of titanium (200-400 nm) deposited by ion beam assisted deposition.

Results

The anodizing process provides a wide variety of colors depending on the voltage applied. The color is typically uniform throughout the surface for most experiments. However, the hydrofluoric acid solutions produce colors only at the meniscus of the solution (when coupons are not fully immersed). Also, several colors develop at the meniscus in these samples. This phenomenon is not observed on samples anodized in the phosphoric and sulfuric acid solutions. The following is a summary of the voltages used and colors obtained.

20% Phosphoric Acid Solution

| Voltage (V) | Color |
| --- | --- |
| 5 | Silver |
| 10 | Dark Gold |
| 20 | Purple |
| 30 | Light Blue |
| 80 | Pink/light gold |
| 90 | Pink/purple |
| 100 | Purple/green |

80% Phosphoric Acid/10% Sulfuric Acid Solution

| Voltage (V) | Color |
| --- | --- |
| 10 | Dark Gold |
| 15 | Brown/gold |
| 20 | Purple |
| 25 | Blue/purple |
| 30 | Dark Blue |
| 40 | Blue |
| 50 | Blue/green |
| 60 | Yellow/green |
| 70 | Yellow/gold |
| 80 | Dull gold |

1.5% Hydrofluoric Acid Solution

| Voltage (V) | Color |
| --- | --- |
| 5 | Multi-color band |
| 20 | Multi-color band |
| 30 | Multi-color band |

A selection of samples are examined on a field-emission SEM, with emphasis on the thicker oxide samples, based on voltages and colors.

Figure 7A:
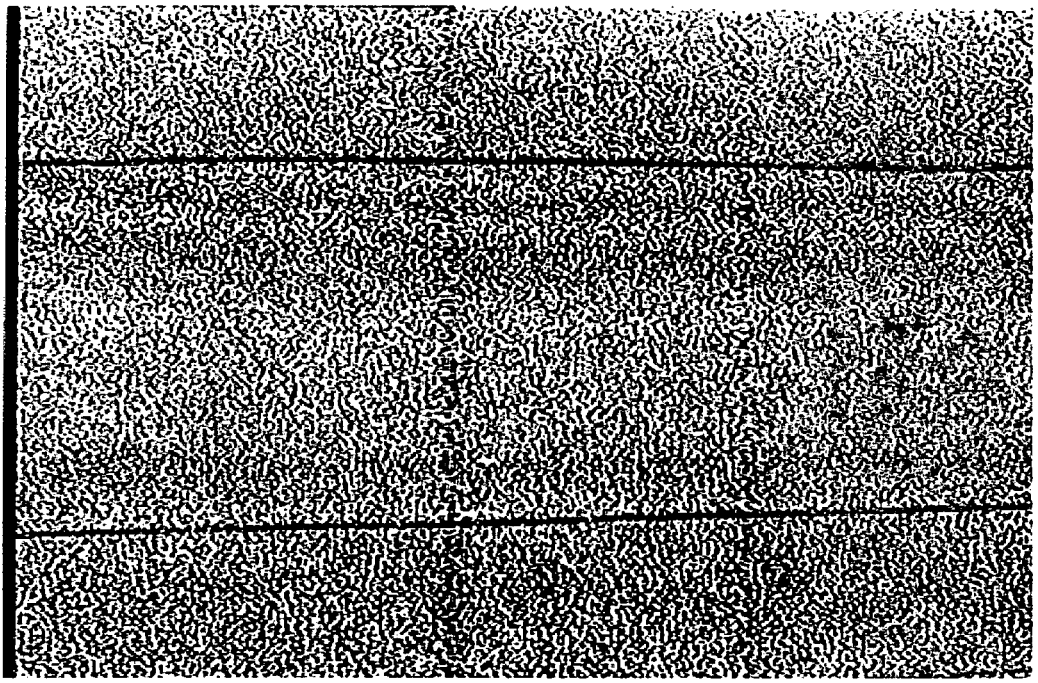
FIG. 7A is a color photograph of a surface morphology.

Referring to FIG. 7A, in the HF solution, uniform color over the completely immersed surface is obtained in the first several seconds but this rapidly redissolves, leaving the multi-colored colored band at the meniscus. The band is approximately 1.5 mm wide and is located between the scribed parallel lines in FIG. 7A.

Figure 7B:
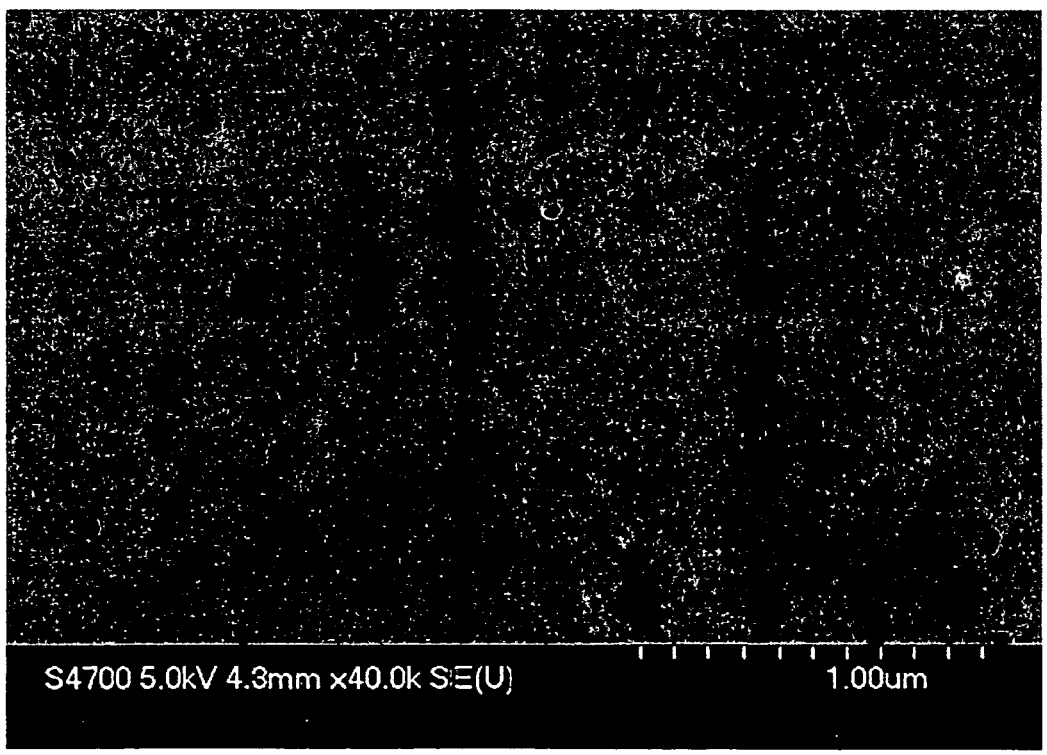
FIG. 7B is a field emission SEM image of a surface morphology.

Referring to FIG. 7B, the sample anodized in the phosphoric acid solution at 90 V reveals a porous structure in the oxide.

Figure 7C:
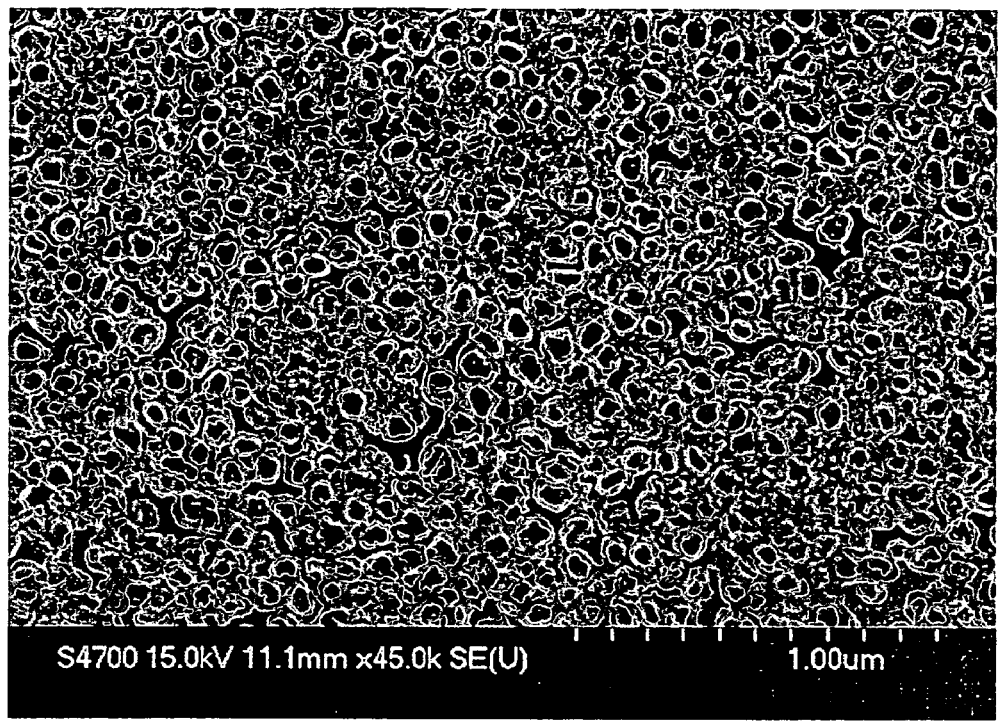
FIG. 7C is a field emission SEM image of a surface morphology.

Referring to FIG. 7C, samples which develop the multi-color bands in the hydrofluoric acid solutions are examined. Each of the different colors within this band is examined separately in order to identify whether they have different structures. Pronounced structure is obtained within the dark green layer at the lower end of the band. This dark green layer reveals a uniform porous structure of hollow post-shaped elements.

Moving upward through the bands of color, the porous structure becomes less pronounced and is at earlier stages of growth or re-dissolution. The structure is observed up to the purple/pink band but beyond that is not detected.

The diameter of the post-shaped elements is approximately in the range of about 70 nm to about 100 nm. Their depth is in the range of about 100 nm to about 200 nm. This measurement can be performed by atomic force microscopy.

Figure 7D:
FIG. 7D is a color photograph of a stent (at 2× magnification).

Referring to FIG. 7D, a comparison between an anodized titanium-coated surface (blue in color) and a non-anodized titanium-coated surface (silver in color) is provided. The titanium-coated stents which are anodized at 80 V and in a 20% phosphoric acid solution show a dark blue color after the treatment. Stents and coupons given this treatment do not reveal a hollow post-shaped porous oxide structure.

Discussion

In phosphoric solutions at high voltages, the titanium oxide has a somewhat non-uniform porosity. When anodized in dilute hydrofluoric acid solutions, a very pronounced, controlled hollow post-shaped porous structure develops. This structure develops at the meniscus where the sample is suspended into the solution. The oxide forms rapidly but rapidly re-dissolves, except at the meniscus, where it develops into a morphology of post-shaped elements. The porous morphology can thus be controlled.

Other Embodiments

While a stent has been described above, a hollow post-shaped morphology and/or color differentiation may be used in other implantable medical devices. For example, it may be used in guidewires, catheters (including balloon angioplasty catheters), or filters (including vena cava filters). In some embodiments, one portion of a medical device includes an anodized metal (e.g., titanium), while another portion of the medical device includes a different anodized metal (e.g., tantalum). The characteristics of a porous layer on one section of a medical device can differ from the characteristics of a porous layer on a different section of the medical device. For example, one section can have larger pores and can contain one type of therapeutic agent (e.g., an antithrombogenic agent), while another section has smaller pores and contains a different type of therapeutic agent (e.g., an anti-inflammatory). Thus, the two different therapeutic agents can be delivered into the body at different rates. In some cases, the porous layer can include a coating that is a therapeutic agent.

All publications, applications, references, and patents referred to above are incorporated by reference in their entirety.

Other embodiments are within the scope of the following claims.

What is claimed is:

1. A stent device comprising:
a generally tubular member, the member including a porous structure comprising an oxide of titanium, niobium, tantalum, or an alloy thereof, the porous structure defined by a plurality of hollow post-shaped elements, the hollow post-shaped elements separated by a void region therebetween and each hollow post-shaped element defining an internal volume adapted to contain a therapeutic agent, wherein the generally tubular member has a longitudinal axis and the generally hollow post-shaped elements have a longitudinal axis generally perpendicular to the longitudinal axis of the generally tubular member.

2. The device of claim 1, wherein the porous structure is of an oxide of titanium.

3. The device of claim 1, wherein the generally tubular member comprises a therapeutic agent contained in the internal volumes, the void region, or a combination thereof.

4. The device of claim 3, wherein the therapeutic agent is selected from an antithrombogenic, antioxidant, anti-inflammatory, antiproliferative, or antibiotic.

5. The device of claim 3, wherein the therapeutic agent is selected from a drug, cell, or genetic material.

6. The device of claim 1, wherein the generally tubular member includes a layer of titanium, niobium, tantalum, or an alloy thereof, that has a thickness between about 50 nm and about 500 nm.

7. The device of claim 6, wherein the porous structure is over said layer.

8. The device of claim 1, wherein the post-shaped elements have inner diameters of about 5 nm to about 200 nm.

9. The device of claim 8, wherein the post-shaped elements have inner diameters of about 70 nm to about 100 nm.

10. The device of claim 9, wherein the post-shaped elements have a post height of about 100 nm to about 200 nm.

11. The device of claim 1, wherein the porous structure is on an outer surface of the generally tubular member.

12. The device of claim 1, wherein the generally tubular member comprises titanium, niobium, tantalum, or an alloy thereof.

13. The device of claim 1, wherein said titanium, niobium, tantalum, or alloy thereof is a layer on a different metal.

14. The device of claim 13, wherein the different metal is about 90% or more of the thickness of the tubular member.

15. The device of claim 1, wherein the generally tubular member comprises stainless steel, nitinol, or a cobalt-based alloy.

16. The device of claim 1, wherein the porous structure includes a polymer.

17. The device of claim 16, wherein the polymer is a coating over the porous structure.

18. The device of claim 17, wherein the coating is a diffusion or protective layer.

19. The device of claim 17, wherein the coating is biodegradable.

20. The device of claim 16, wherein the polymer includes a therapeutic agent.

21. The device of claim 1, wherein the porous structure includes a colorant.

22. The device of claim 1, wherein the device has a color corresponding to light having a wavelength between about 370 nm and about 750 nm.

23. The device of claim 22, wherein the color corresponds to light having a wavelength of about 420 nm, about 470 nm, about 530 nm, about 580 nm, about 620 nm, or about 700 nm.

24. The device of claim 1, wherein the hollow post-shaped elements are generally tubular.

25. The device of claim 1, wherein the porous structure has a post-shaped element density of 10 to 300 post-shaped elements per square micron.

26. The device of claim 1, wherein the porous structure acts as a grating that preferentially reflects light having a wavelength between 370 nm and 750 nm.

27. The device of claim 1, wherein the hollow post-shaped elements comprise a closed end.

28. A stent device comprising:
a generally tubular member, the member including a porous structure defined by an plurality of hollow post-shaped elements, the hollow post-shaped elements separated by a void region and each hollow post-shaped element defining an internal volume adapted to contain a therapeutic agent, wherein the generally tubular member has a longitudinal axis and the generally hollow post-shaped elements have a longitudinal axis generally perpendicular to the longitudinal axis of the generally tubular member.

29. The device of claim 28, wherein the generally tubular member includes a therapeutic agent contained in the internal volumes, the void region, or a combination thereof.

30. The device of claim 29, wherein the therapeutic agent is selected from an antithrombogenic, antioxidant, anti-inflammatory, antiproliferative, or antibiotic.

31. The device of claim 29, wherein the therapeutic agent is selected from a drug, cell, or genetic material.

32. The device of claim 28, wherein the post-shaped elements comprise a porous metal oxide.

33. The device of claim 32, wherein the porous metal oxide has a thickness between about 50 nm and about 500 nm.

34. The device of claim 32, wherein the porous metal oxide is on a surface of the generally tubular member.

35. The device of claim 28, wherein the post-shaped elements have inner diameters between about 5 nm and about 200 nm.

36. The device of claim 28, wherein the hollow post-shaped elements are generally tubular.

37. The device of claim 28, wherein the porous structure has a post-shaped element density of 10 to 300 post-shaped elements per square micron.

38. The device of claim 28, wherein the porous structure acts as a grating that preferentially reflects light having a wavelength between 370 nm and 750 nm.

39. The device of claim 28, wherein the hollow post-shaped elements comprise a closed end.

* * * * *

UNITED STATES PATENT AND TRADEMARK OFFICE
CERTIFICATE OF CORRECTION

PATENT NO. : 7,488,343 B2  
APPLICATION NO. : 10/664679  
DATED : February 10, 2009  
INVENTOR(S) : Barry O'Brien Page 1 of 1

It is certified that error appears in the above-identified patent and that said Letters Patent is hereby corrected as shown below:

Column 15, line 16 (Claim 28), please delete "an" and insert --a-- therefor.

Signed and Sealed this

Fourteenth Day of July, 2009

JOHN DOLL  
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,488,343 B2 | Page 1 of 1 |
| APPLICATION NO. | : 10/664679 | |
| DATED | : February 10, 2009 | |
| INVENTOR(S) | : Barry O'Brien | |

It is certified that error appears in the above-identified patent and that said Letters Patent is hereby corrected as shown below:

On the Title page,

[*] Notice:  Subject to any disclaimer, the term of this patent is extended or adjusted under 35 USC 154(b) by (762) days Delete the phrase "by 762 days" and insert -- by 1083 days --

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,488,343 B2  Page 1 of 1
APPLICATION NO. : 10/664679
DATED : February 10, 2009
INVENTOR(S) : Barry O'Brien It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1084 days.

Signed and Sealed this

Second Day of November, 2010

David J. Kappos
*Director of the United States Patent and Trademark Office*